United States Patent [19]

Gauthier

[11] 4,010,741
[45] Mar. 8, 1977

[54] SURGICAL RETRACTOR

[76] Inventor: William Kohlmann Gauthier, 310 Codifer Blvd., Metairie, La. 70005

[22] Filed: Jan. 22, 1976

[21] Appl. No.: 651,267

[52] U.S. Cl. .............................................. 128/20
[51] Int. Cl.² ......................................... A61B 17/02
[58] Field of Search ........................... 128/20, 303 R

[56] References Cited

UNITED STATES PATENTS

| | | | |
|---|---|---|---|
| 2,670,732 | 3/1954 | Nelson | 128/20 |
| 3,040,739 | 6/1962 | Grieshaber | 128/20 |

*Primary Examiner*—Robert W. Michell
*Assistant Examiner*—Henry S. Layton
*Attorney, Agent, or Firm*—Shoemaker and Mattare, Ltd.

[57] ABSTRACT

A surgical retractor for use in certain types of deep abdominal surgery wherein it is necessary to remove the intestines from the abdominal cavity, includes an extension releasably secured to a frame and having a retractor arm carried by the extension in an elevated position relative to the frame, to thereby provide space for the intestines draped over the frame, and a retractor blade carried by the arm and engaged with the intestines to retain them out of the abdominal cavity.

7 Claims, 5 Drawing Figures

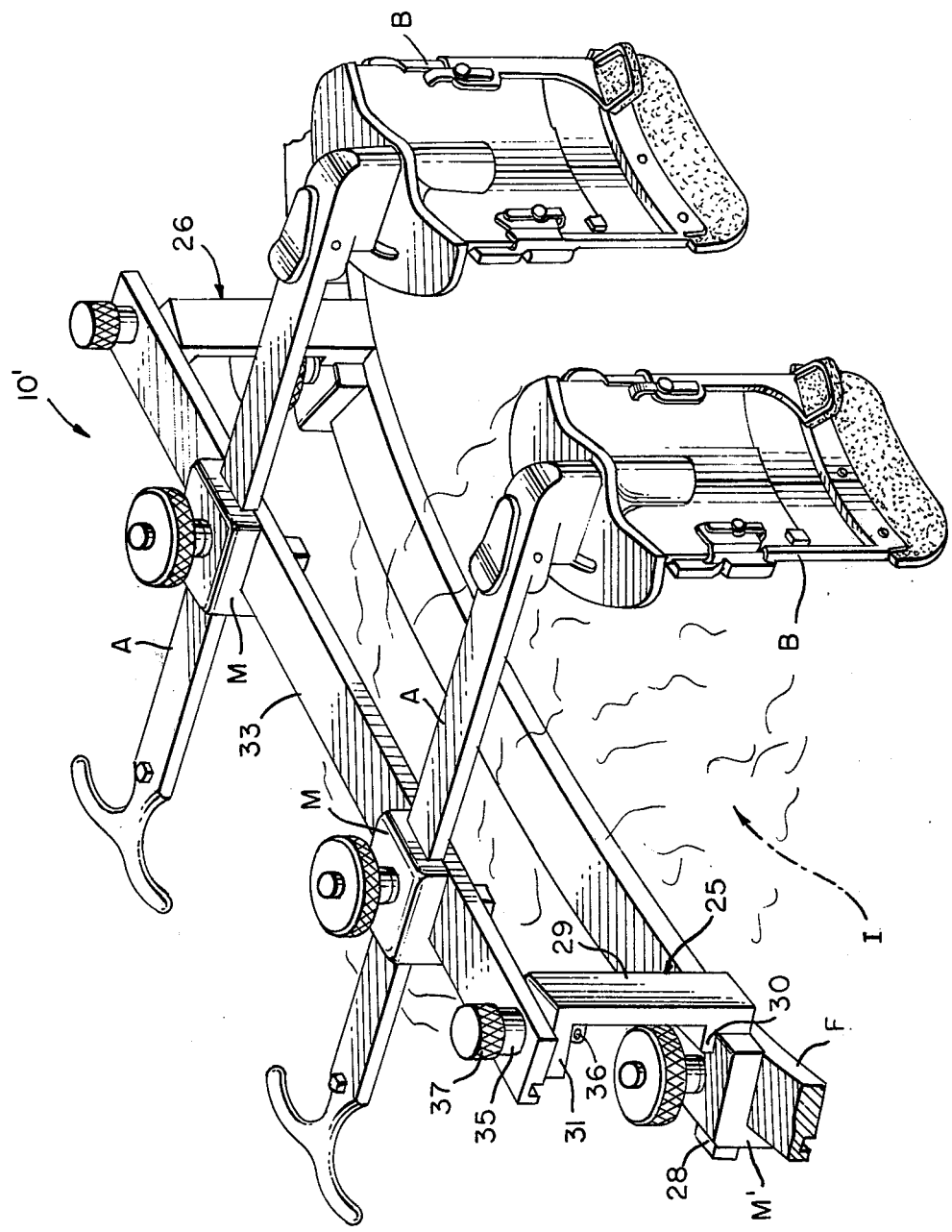

SURGICAL RETRACTOR

BACKGROUND OF THE INVENTION

This invention comprises an improvement over the invention described and claimed in applicant's copending application Ser. No. 515,857, filed Oct. 18, 1974 and now U.S. Pat. No. 3,965,890.

The retractor described in the aforesaid patent application is designed to hold open an incision and to retain the bowel or intestines in the abdominal cavity, and for its intended purpose, the aforesaid surgical retractor performs exceptionally well.

However, in some kinds or types of deep abdominal surgery, such as a resection and excision of large bowel, or where kidneys are removed through an abdominal incision rather than through a flank incision, or in a deep abdominal incision for a lumbar sympathectomy or in vascular surgery for correction of aneurysms or blood clots or constricted areas of the large arteries and veins, it is necessary to remove the intestines from the abdominal cavity and drape them to one side thereof in order to provide adequate access to the working area. In such types of surgery, the surgical retractor described in the aforesaid patent application is not entirely satisfactory, since although it functions exceptionally well to retain the walls of the abdomen open or spread at the incision, the individual blades theeof which are normally applied to retract the intestines back into the abdominal cavity cannot be used, since the intestines must be removed from the cavity and draped to one side, and thus they are in the way of attachment of the retractor arm in the aforesaid application to the frame. Moreover, in the prior art it is necessary during such surgery for someone on the operating team to hold the exposed bowel and messentery out of the way during the surgical procedure. This is typically done either with the hands or with deaver retractors. It is readily apparent that such a procedure is difficult and inefficient, even for relatively quickly performed surgery, and when an operation or surgical procedure is long and drawn out, the procedure necessarily followed in the prior art is entirely unsatisfactory.

With the present invention, on the other hand, an extension is applied to the conventional retractor frame of the type disclosed, for example, in the aforesaid patent application, and a conventional retractor arm and ratchet means also of the type described in the aforesaid patent application are then applied to the extension in an elevated position above the frame, leaving a space between the arm and frame in which the intestines may be placed, and the retractor arm may then be retracted, with a blade carried thereby engaging the intestines to retain them in position out of the abdominal cavity. This arrangement is far superior to the prior art methods, wherein the intestines are either hand held or held with deaver retractors, and moreover, with the present invention more than one retractor blade can be attached to the extension or extensions and engaged with the gathered together intestines, thus reducing the possibility of damage to the intestines and also freeing operating personnel for other duties during a surgical procedure.

OBJECTS OF THE INVENTION

Accordingly, it is an object of this invention to provide a surgical retractor which includes means for supporting a retractor arm in a manner to enable intestines to be removed from the abdominal cavity and draped over the frame of the retractor in a manner such that a retractor blade carried by the arm can engage the intestines to retain them out of he abdominal cavity.

BRIEF DESCRIPTION OF THE DRAWINGS

FIG. 3 is a side view in elevation of the device of FIG. 2.

FIG. 4 is an enlarged, fragmentary, perspective view of a portion of a surgical retractor with a modified form of the invention applied thereto.

FIG. 5 is a side view in elevation of one of the extension pieces of the device of FIG. 4, showing the manner in which it is connected to a conventional frame.

DETAILED DESCRIPTION OF THE PREFERRED EMBODIMENTS

Figure 1:
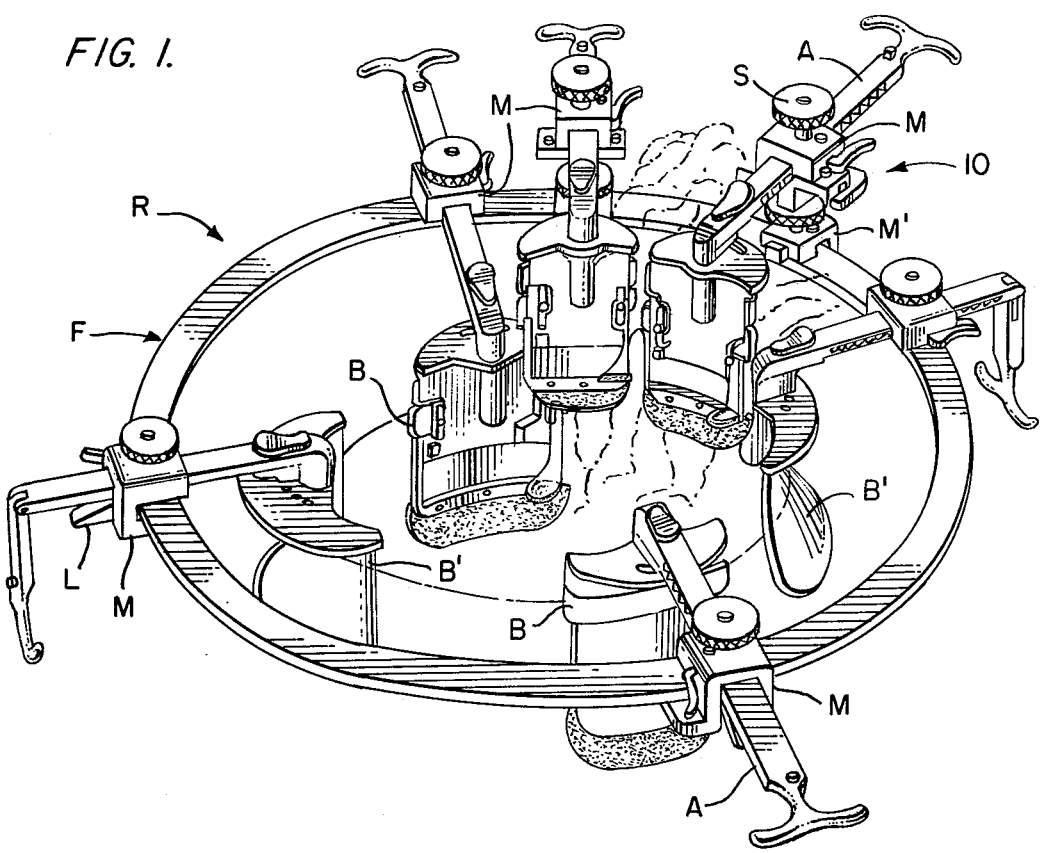
FIG. 1 is a perspective view of a surgical retractor embodying a preferred form of the invention.

In the drawings, wherein like reference numerals indicate like parts throughout the several views, a surgical retractor R includes a closed, generally oval-shaped, one-piece frame F having a plurality of retractor arm mounting means or members M mounted thereto for movement therealong, and a plurality of retractor arm means A carried by the mounting members M for movement of the arms both along the frame with the mounting members and transversely of the frame.

A plurality of retractor blades, including the collapsible type B and balfour blades or tailpieces B', are carried by the arms A and depend from them into the opening defined by the frame for engagement with the flesh about the edge of an incision to hold the flesh out of the way of a surgeon performing an operation.

The frame, mounting means or members, retractor arms and blades may be of the type fully disclosed in applicant's co-pending application Ser. No. 515,857, or in applicant's U.S. Pat. No. 3,749,088.

In addition to the conventional retractor means noted above, the present invention includes one or more extensions 10, preferably formed of extruded aluminum or the like and having a generally Z-shaped configuration in side elevation, with a horizontally extending bottom portion or leg 11 having an upturned lip 12 on the free outer end thereof, and joined to a first vertically extending riser portion 13, having a rib or ledge 14 on the inner surface thereof extending over the bottom portion 11 toward the upturned lip 12. A second horizontally extending portion or intermediate section 15 extends from the upper end of the first riser portion 13 over and parallel to the bottom portion 11 and terminates at its end in a second vertically extending riser portion 16. The second horizontal portion or intermediate portion 15 is shorter in length than the bottom portion 11, and has a plurality of serrations 17 on the upper surface thereof adjacent the shoulder or junction with first riser portion 13 to provide a finger gripping surface or roughened area to facilitate manipulation thereof during use. A third or upper horizontally extending portion 18 includes oppositely extending, laterally directed flanges 19 and 20, having a cross-sectional configuration substantially identical to the cross-sectional configuration of the frame F and including a channel 21 in the underside thereof near the forward edge 22. A pair of upstanding pins or detents 23 and 24 are provided on the upper surface of the top portion 18 near the opposite ends thereof.

A somewhat modified mounting member M' is assembled to the bottom horizontal portion 11, and is engaged between the upturned lip 12 and the ledge or rib 14 and is normally not removable from the bottom member or portion 11. In use, the lever L carried by the mounting member M' is elevated and the mounting member M' is attached to the frame F, as illustrated, for example, in FIG. 3. The lever L is then released and the mounting member M' with the extension 10 is thus assembled to the frame.

A retractor arm A, having a conventional mounting member M of the type described in the aforesaid patent is then assembled to the top portion 18 of the extension 10 identically to the manner in which the arm and mounting member are normally attached to the frame F, and the pins 23 and 24 prevent the mounting member M and retractor arm from being accidentally displaced from the extension during use.

Thus, as seen best in FIGS. 1 and 3, the retractor arm A is maintained in an elevated postion relative to the frame F and a plurality of these extensions and associated retractor arms may be placed on the frame, with the intestines gathered together and draped over the frame between one or more of the extensions, and the retractor arms then retracted with the blades B carried thereby engaging the intestines to retain them out of the abdominal cavity.

Figure 2:
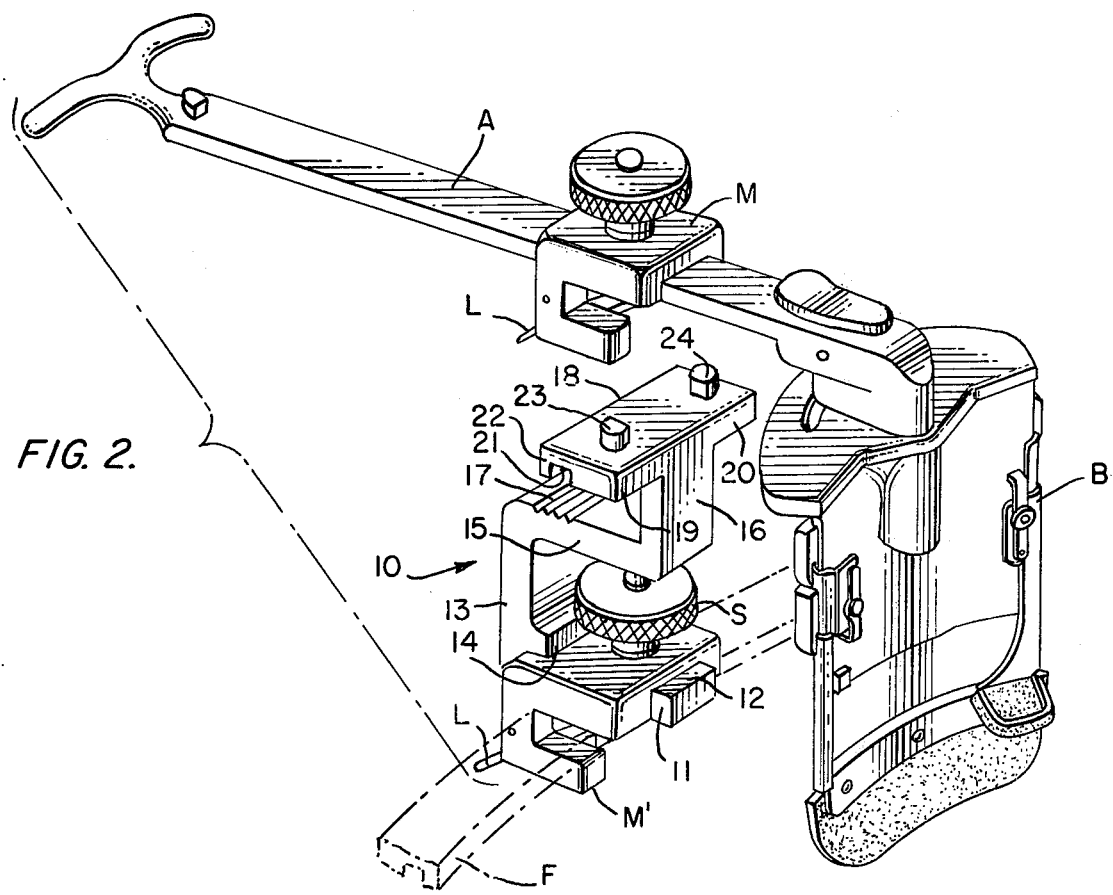
FIG. 2 is an exploded, perspective view of one of the extensions and a retractor arm associated therewith in accordance with the preferred form of the invention.

In FIGS. 4 and 5, a modified form of intestinal retractor 10' includes a pair of extensions 25 and 26, each having a substantially L-shaped configuration in side elevation, and including a bottom leg 27 having an upturned lip 28 on the outer end thereof, as in the previously described embodiment, and a vertically extending leg 29 with an inwardly directed flange or rib 30 thereon extending over the bottom leg 27 toward the upturned lip 28 in a manner to engage an adjacent upper edge portion of a mounting member M' assembled thereto identically to that described in connection with the preferred form of the invention in FIGS. 1, 2 and 3. A second, relatively short, horizontally extending upper leg 31 extends from the upper end of the vertical leg 29 a short distance over the bottom leg 27. A threaded opening 32 is formed through the top leg 31, and a substantially straight, elongate mounting bar 33, having a cross-sectional configuration substantially identical to the cross-sectional configuration of the frame, includes a pair of openings 34 therethrough adjacent the opposite ends thereof. A retaining screw 35, having a threaded extension 36 on the lower end thereof and a knurled upper end 37, is then extended through the openings 34 in the bar 33, and into the threaded opening 32 in the top leg 31 of extension 10' to retain the mounting bar 33 in spanning relationship between a pair of extensions 25 and 26. One or more retractor arms A and mounting members M, with associated retractor blades B, may then be assembled to the mounting bar 33, as depicted, for example, in FIG. 4, with the retractor blades B engaged with intestines I draped over the frame F in the space provided between the upstanding extensions 25 and 26 and the frame F and mounting bar 33 carried by the extensions.

In both forms of the invention, the thumbwheels or screws S may be tightened after the retractor arms and blades have been properly positioned to maintain them in their desired adjusted positions.

While the invention has been particularly described with reference to a specific type of retractor frame and associated retractor arms and mounting members, it should be understood that the inventive concept could equally as well be applied to other surgical retractor constructions which include retractor means for holding open an incision.

Further, the frame, arm, blade means and mounting means may comprise extruded aluminum or the like, or other suitable material, and the extensions may also comprise similar or like materials.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A surgical retractor for use in surgery to hold an incision open and to retain intestines out of the way to provide working area for performing a surgical procedure, comprising: a frame means; a plurality of retractor arm means releasably carried by the frame means for movement along the frame means and for movement transversely of the frame means, and including retractor blade means carried by the arm means in a position to be disposed in an incision to engage the flesh at the edge of the incision to hold the incision open; extension bottom mounting member releasably carried by the frame means for movement along the frame means; upstanding extension means carried by the extension mounting member for movement therewith and extending above the plane of the frame means and including an upper mounting member connecting said arm means to said extension means, said mounting member being substantially similar to said extension mounting member, whereby said mounting member can connect said arm means to either said frame means or said upstanding extension means; further retractor arm means carried by the extension means in an elevated position above the plane of the frame means, thus providing a space between the further retractor arm means and the frame means, in which intestines removed from the abdominal cavity through the incision may be placed; and blade means carried by the further retractor arm means in a position to engage the intstines and retain them out of the abdominal cavity to provide working area for a surgical procedure.

2. A surgical retractor as in claim 1, wherein the extension means comprises: an upstanding member having a bottom end and an upper end and an intermediate, riser portion connecting the bottom end and upper end; said bottom end carrying said bottom mounting member which has means for releasable attachment to the frame means; and said further retractor arm means carried by the upper mounting member for movement transversely of the frame means.

3. A surgical retractor as in claim 2, wherein said intermediate, riser portion has a roughened surface on a portion thereof comprising a finger gripping surface to facilitate manipulation thereof during use.

4. A surgical retractor as in claim 3, wherein the extension means comprise: a one-piece body having a generally Z-shaped configuration in side elevation, and including a substantially horizontal bottom member adapted to overlie the frame means and on which the bottom mounting member is carried, a first, intermediate riser portion extending substantially vertically from one end of the bottom member and terminating at its upper end in one end of a generally horizontally extending intermediate portion extending over the bottom portion in spaced relation thereto, a second substantially vertically extending riser portion extending upwardly from the other end of the horizontal intermediate portion and terminating at its upper end in an upper, generally horizontally extending portion on which the upper mounting member and retractor arm are carried.

5. A surgical retractor as in claim 1, wherein the extension means comprises a pair of extension members carried by the frame means in spaced apart relation to one another, and a retractor arm mounting bar is connected adjacent its opposite ends to the spaced apart extension members and extends therebetween in spanning relation thereto; and said further retractor arm means is carried by the mounting bar.

6. A surgical retractor as in claim 5, wherein the extension members are each substantially L-shaped in side elevation and each includes a generally horizontal bottom leg and a generally vertical leg, with a short, horizontally extending flange on the upper end of the vertical leg, said extension mounting member carried by the bottom leg, and said mounting bar releasably secured to said flange on the upper end of the vertical leg.

7. A surgical retractor as in claim 6, wherein said mounting bar has a cross-sectional configuration substantially the same as the cross-sectional configuration of the frame means, whereby the same retractor arm means and retractor arm mounting means may be used interchangeably on the frame means and on the mounting bar.

* * * * *